(12) United States Patent
Viöl et al.

(10) Patent No.: US 12,159,769 B2
(45) Date of Patent: Dec. 3, 2024

(54) DEVICE FOR FORMING PHYSICAL PLASMA ON A SURFACE OF AN OBJECT

(71) Applicant: Hochschule für angewandte Wissenschaft und Kunst Hildesheim/Holzminden/Goettingen, Hildesheim (DE)

(72) Inventors: Wolfgang Viöl, Adelebsen (DE); Thomas Borchardt, Duderstadt (DE); Joachim Bertram, Niemetal (DE)

(73) Assignee: Hochschule für angewandte Wissenschaft und Kunst Hildesheim/Holzminden/Goettingen, Hildesheim (DE)

( * ) Notice: Subject to any disclaimer, the term of this patent is extended or adjusted under 35 U.S.C. 154(b) by 151 days.

(21) Appl. No.: 17/723,945

(22) Filed: Apr. 19, 2022

(65) Prior Publication Data

US 2022/0238308 A1    Jul. 28, 2022

Related U.S. Application Data

(63) Continuation of application No. PCT/EP2020/079316, filed on Oct. 19, 2020.

(30) Foreign Application Priority Data

Oct. 22, 2019    (DE) .................... 10 2019 128 538.0

(51) Int. Cl.
*H01J 37/00* (2006.01)
*A61N 1/32* (2006.01)
(Continued)

(52) U.S. Cl.
CPC ........ *H01J 37/32348* (2013.01); *A61N 1/328* (2013.01); *H05H 1/2418* (2021.05);
(Continued)

(58) Field of Classification Search
CPC ... H01J 37/32348; A61N 1/328; A61N 1/322; A61N 1/0408; H05H 1/2418
See application file for complete search history.

(56) References Cited

U.S. PATENT DOCUMENTS

| | | | |
|---|---|---|---|
| 11,253,695 B2* | 2/2022 | Kreis | ................. A61N 1/36017 |
| 2011/0180732 A1 | 7/2011 | Hirasawa et al. | |

(Continued)

FOREIGN PATENT DOCUMENTS

| | | |
|---|---|---|
| DE | 102011050631 A1 | 11/2012 |
| DE | 102015112200 A1 | 2/2017 |

(Continued)

OTHER PUBLICATIONS

English Translation of PCT International Preliminary Report on Patentability in co-pending, related PCT Application No. PCT/EP2020/079316, mailed Apr. 26, 2022.

*Primary Examiner* — Tuan T Lam
(74) *Attorney, Agent, or Firm* — Thomas | Horstemeyer, LLP

(57) ABSTRACT

A device serves for generating physical plasma by means of dielectric barrier discharges with respect to a surface of an object. The device comprises a common high voltage terminal, and a plurality of electrode bodies that are capacitively coupled to the common high voltage terminal, that comprise an exposed electrode surface and a distal end each, and that are, in a main extension direction, elongated in parallel to one another towards their distal ends. The device further comprises spacers made of dielectric a d arranged at the distal ends of the electrode bodies, the spacers projecting beyond the exposed electrode surfaces of the electrode bodies by 1.0 mm to 5.0 mm in the main extension direction. The device may be part of a hair loss therapy apparatus.

16 Claims, 4 Drawing Sheets

(51) Int. Cl.
*H01J 37/32* (2006.01)
*H05H 1/24* (2006.01)
*A61N 1/04* (2006.01)

(52) U.S. Cl.
CPC ............ *A61N 1/0408* (2013.01); *A61N 1/322* (2013.01); *H05H 2245/30* (2021.05)

(56) References Cited

U.S. PATENT DOCUMENTS

| | | | |
|---|---|---|---|
| 2013/0060246 A1* | 3/2013 | Knopp | A61N 1/05 606/41 |
| 2016/0354614 A1 | 12/2016 | Watson et al. | |
| 2019/0105506 A1 | 4/2019 | Bourquin et al. | |
| 2019/0217080 A1* | 7/2019 | Moss | A61N 1/40 |
| 2020/0038530 A1* | 2/2020 | Yildirim | A61H 7/005 |
| 2020/0069957 A1 | 3/2020 | Kim | |
| 2020/0084871 A1 | 3/2020 | Kim | |
| 2021/0385935 A1 | 12/2021 | Wandke et al. | |
| 2022/0399096 A1* | 12/2022 | Zucker | A61B 34/32 |
| 2023/0301552 A1* | 9/2023 | Mallires | A61B 5/16 600/345 |

FOREIGN PATENT DOCUMENTS

| | | |
|---|---|---|
| DE | 102018126489 A1 | 4/2020 |
| DE | 102018126492 A1 | 4/2020 |
| EP | 2308552 A1 | 4/2011 |
| EP | 2713807 A1 | 4/2014 |
| EP | 3329747 A1 | 6/2018 |
| WO | 2017162505 A1 | 9/2017 |
| WO | 2018004300 A1 | 1/2018 |
| WO | 2018190499 A1 | 10/2018 |
| WO | 201910714 | 6/2019 |
| WO | 2020083992 A1 | 4/2020 |

\* cited by examiner

DEVICE FOR FORMING PHYSICAL PLASMA ON A SURFACE OF AN OBJECT

CROSS REFERENCE TO RELATED APPLICATIONS

This application is a continuation of International Application PCT/EP2020/079316 with an international filing date of Oct. 19, 2020 and claiming priority to co-pending German Patent Application No. DE 10 2019 128 538.0 entitled "Vorrichtung zum Ausbilden von physikalischem Plasma an einer Oberfläche eines Objekts", filed on Oct. 22, 2019.

FIELD OF THE INVENTION

The present invention generally relates to a device for generating physical plasma at a surface of an object.

BACKGROUND OF THE INVENTION

A device for generating dielectric barrier discharges with respect to a surface of the object, the device comprising a high voltage terminal and a plurality of electrode bodies that are capacitively coupled to the high voltage terminal, that have exposed electrode surfaces, and that elongated in parallel to each other towards distal ends, is known from German patent application publication DE 10 2011 050 631 A1 and European patent EP 2 713 807 B1 belonging to the same patent family. Here, the plurality of electrode bodies made of metal are coupled to the high voltage terminal in that they are facing a high voltage bus connected to the high voltage terminal with a dielectric solid body arranged in between. Practically, for this purpose, the plurality of electrode bodies proximally end within the dielectric solid body, and the high voltage bus comprises a metal sheet enclosing the proximal ends of the electrode bodies within the dielectric solid body in an U-shape. With their directions of main extension, the electrode bodies are in one plane, wherein their distal ends are arranged in a line with a steady course. By means of the known device, electric discharges may be generated with respect to an earthed object, which start from the distal ends of the electrode bodies. At or close to a human scalp, the electric discharges are generated for killing parasites, like for example hair lice and their preforms, i.e. nits and larvae.

A device for generating physical plasma by means of dielectric barrier discharges with respect to a surface of a body, in which individual, practically three deformable electrode bodies shielded with dielectric are provided to bring them into contact with the surface of the object to be treated, is known from international patent application publication WO 2018/004300 A1. The electrode bodies are arranged within a ring-shaped counter-electrode. The known device is provided for treating hair loss, and, for this purpose, it is brought into contact with the curved scalp of the patient. The plasma generated by means of the dielectric barrier discharges arises in the area of small distances between the scalp and the dielectric barriers of the electrode bodies pressed against the scalp. In this known device, the individual electrode bodies with their dielectric barriers are of complex design, and the device only allows for a very local generation of plasma and thus only for a very local treatment with the plasma.

A device for treating hair loss which forms a chamber above the scalp of the respective patient by means of a helmet, is known from US patent application publication US 2016/0354614 A1. A cold plasma generated by means of dielectric barrier discharges is fed into this chamber. This known device is of a very complex overall construction.

A device for treating skin with cold plasma is known from international patent application publication WO 2017/162505 A1 and patent application publication US 2019/0105506 A1 belonging to the same patent family. The device comprises a housing with an end face, a generator for generating cold plasma which provides reactive species for treating the skin, and a manipulator for manipulating the skin in order to increase the exposition of bacteria on the skin to the reactive species in the use of the device. Within the use, the generator is arranged at an essentially always constant distance to the skin. During the use, the manipulator extends between the generator and the skin, and it includes a movable element which is configured for contacting the skin during the use of the device. The manipulator may have a plurality of protrusions which are configured for contacting the skin during the use of the device. The generator and the manipulator may be made in one piece, the manipulator being arranged on a surface of the generator.

An electrode arrangement for a surface treatment of a body with a physical plasma is known from German patent application publication DE 10 2015 112 200 A1 and European patent EP 3 329 747 B1 belonging to the same patent family. The electrode arrangement comprises a high voltage terminal for connection to an output of an alternating high voltage source, a plurality of line-shaped electrode bodies which are connected to the high voltage terminal and which are enclosed by a dielectric, and which are individually capacitively coupled to the high voltage terminal, and a treatment space adjoining the electrode bodies, into which the body is to be introduced for the plasma treatment. Each of the electrode bodies includes an arc-shaped area in which the respective line-shaped electrode body changes its direction by at least 90°. The treatment space is at least partially arranged between the arc-shaped areas of the electrode bodies.

A plasma treatment device which is configured for treating a surface with a dielectric barrier plasma is known from German patent application publication DE 10 2018 126 492 A1 and US patent application publication US 2021/385935 A1 belonging to the same patent family. The plasma treatment device comprises a base body which has a treatment side of two dimensional extension that is turned towards the surface to be treated, an electrode arrangement including at least one electrode, and a dielectric which completely covers the at least one electrode towards the surface to be treated. A high voltage signal may be applied to the electrode via a high voltage feeding line. A nub arrangement on the treatment side of the base body which comprises a plurality of nubs allows for a combination of an effective plasma treatment with an effective mechanical treatment in that the at least one electrode of the electrode arrangement extends into at least one nub of the nub arrangement.

A further plasma treatment device for treating a surface with a dielectric barrier plasma comprising an electrode arrangement having at least one electrode, a dielectric which completely covers the electrode towards the surface to be treated, and a housing is known from German patent application publication DE 10 2018 126 489 A1 and international patent application publication WO 2020/083992A1 belonging to the same patent family, which have both been published after the priority date of the present application. A high voltage signal can be applied to the electrode via a high voltage feeding line. The combination of an effective plasma treatment with an effective mechanical treatment of the surface to be treated is here enabled in that the plasma treatment device has a brush head which has a bristle field and a bristle carrier with a base face. The bristle field comprises a plurality of flexible bristles and interspaces between the bristles. The bristles extend away from the base face of the bristle carrier towards a support face which is defined by the ends of the longest bristles of the bristle field facing away from the base face.

There still is a need of a device for generating physical plasma by means of dielectric barrier discharges, which has a simple construction and which is nevertheless well suited for generating physical plasma over larger areas of a scalp of a human in order to treat hair loss or stimulate hair growth.

SUMMARY OF THE INVENTION

The present invention relates to device for generating physical plasma by means of dielectric barrier discharges with respect to a surface of an object. The device comprises a common high voltage terminal, and a plurality of electrode bodies that are capacitively coupled to the common high voltage terminal, that comprise an exposed electrode surface and a distal end each, and that are, in a main extension direction, elongated in parallel to one another towards their distal ends. The device further comprises spacers made of dielectric and arranged at the distal ends of the electrode bodies, the spacers projecting beyond the exposed electrode surfaces of the electrode bodies by 1.0 mm to 5.0 mm in the main extension direction.

The invention further relates to a hair loss therapy apparatus comprising such a device.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
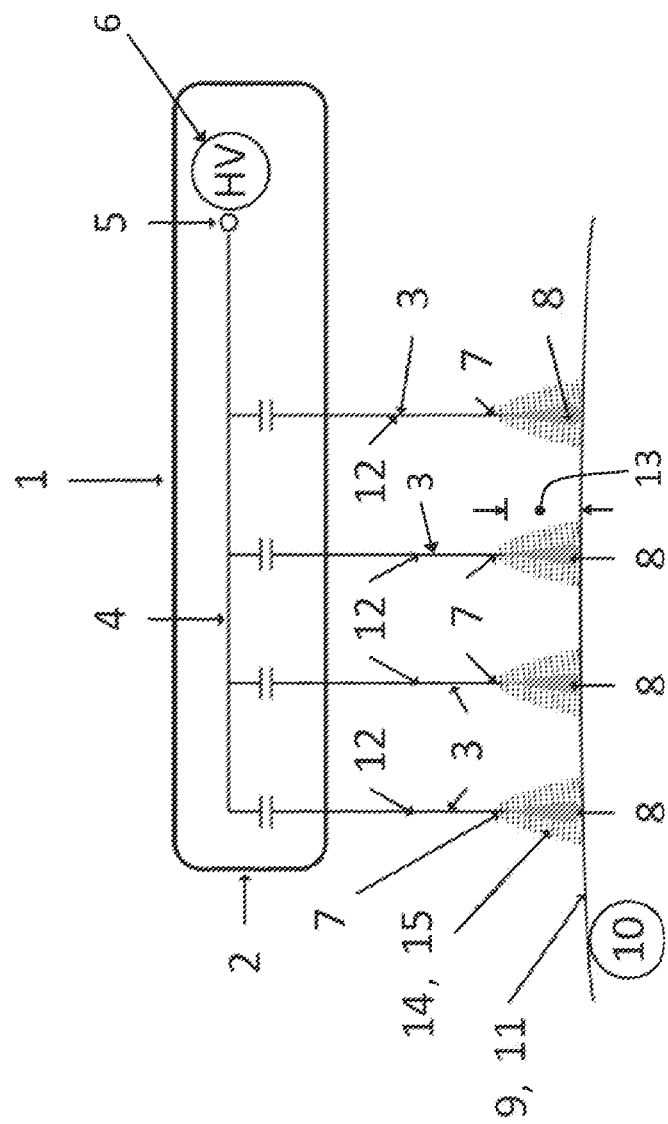
FIG. 1, in a schematic depiction, shows a device according to the invention in treating a scalp.

In a device for generating physical plasma by means of dielectric barrier discharges with respect to a surface of an object, the device comprising a common high voltage terminal and a plurality of electrode bodies that are capacitively coupled to the common high voltage terminal, that have exposed electrode surfaces and that are elongated in parallel to one another towards distal ends, spacers made of dielectric are arranged at the distal ends of the electrode bodies, which, in a main extension direction of the electrode bodies, extend by 1.0 mm to 5.0 mm beyond the exposed electrode surfaces of the electrode bodies.

In the device, the electrode bodies, by means of the spacers made of dielectric, are not provided with a dielectric barrier which dielectrically restrains the electric discharges generated by applying a high voltage to the electrode bodies. In the device, the dielectric restraint to the discharges is based on the capacitive coupling of the electrode bodies to the high voltage terminal. When the spacers made of dielectric contact the surface of the respective object, the spacers rather provide for a defined distance between the exposed electrode surfaces of the electrode bodies and the surface to be treated. This results into defined discharge gaps between the exposed electrode surfaces and the surface to be treated, across which the desired physical plasma is generated under defined conditions by means of the dielectric barrier discharges. The effective height of the spacers of 1.0 to 5.0 mm limits the high voltage necessary for igniting electric discharges and, thus, the irritations of the surface, for example a human scalp, caused by these high voltages. At the same time, both an electrical short towards the surface and a strongly locally limited discharge area are avoided. Further, the spacers made of dielectric protect the surface to be treated against a mechanical stress by means of the electrode bodies. Thus, even with electrode bodies of small diameter made of metal, there is no danger of a scratching damage to the surface.

In the device, the spacers may be placed on top of the distal ends of the electrode bodies, or they may enclose the distal ends of the electrode bodies. The latter construction increases the contact area between the spacers and the electrode bodies and thus improves the stability of the connection between the spacers and the electrode bodies.

The spacers may be spherical or drop-shaped. Practically, the spacers may be formed by temporarily dipping the distal ends of the electrode bodies into a melt of the respective dielectric, subsequently forming the spacers from the adhering melt by means of the surface tension of the melt, and finally curing the dielectric. The spacers may, however, not only be made of meltable plastics but also of any other dielectric materials. In any case, spherical or drop-shaped spacers at the distal ends of the electrode bodies serve for a high protection of the surface to be treated against injuries caused by the electrode bodies.

Besides the shape, the protection by means of the spacers against injuries is also determined by surface curvature radiuses of the spacers. The spacers may end with surface curvature radiuses which are at least as long as a diameter of the respective electrode body in the area of its exposed electrode surface. An upper limit to the surface curvature radiuses of the spacers is about three times the diameter of the respective electrode body in the area of its exposed electrode surface. Then, a spherical electrode body has a diameter with is six times as long as the diameter of the electrode bodies.

In the area of their exposed electrode surfaces, the electrode bodies may have a diameter in a typical range of 0.5 mm to 2.5 mm. If the electrode bodies are, for example, made of metal, their diameters, besides the modulus of elasticity of the metal, determines the bending stiffness of the electrode bodies. The transverse stiffness of the electrode bodies with respect to deviations of the spacers arranged at their free ends also depends on the length of the electrode bodies. These lengths are in a typical range from 5.0 mm to 50 mm. All at all, the electrode bodies may be elastic and support the spacers with bending stiffnesses in a range from 600 $Nmm^2$ to 4,000 $Nmm^2$. In this way, the positions of the spacers are still sufficiently defined but they may nevertheless give way in case of contact with obstacles. Due to this ability for giving way, the dangers of damages to the electrode bodies or the spacers or of the spacers or getting loose from the electrode bodies are strongly limited.

Lateral distances between the electrode bodies are in a typical range from 2.0 mm to 20 mm. At exactly these lateral distances, the spacers may be arranged in a one dimensional array along a straight line or a line with a steady course. Such a steady line has no steps and preferably also no kinks. In this embodiment, the device is similar to a comb whose tines are formed by the electrode bodies.

In a brush-like embodiment of the device, the spacers are arranged in a two dimensional array along a plane or an area with a steady course. Such a steady area preferably also has neither steps nor kinks. However, the steady area may, for example, be concavely curved in two dimensions so that the spacers at the distal ends of the electrode bodies may get into a large area contact with a scalp.

The electrode bodies may be supported or mounted within a base body of the device and, in the area of their support, they may be individually capacitively coupled to the common high voltage terminal. An individual coupling of the electrode bodies to a high voltage bus which is connected to the common high voltage terminal is preferred.

The high voltage terminal may in turn be connected to an output of a high voltage generator of the device, at which the high voltage generator outputs a pulsed high voltage with respect to earth. With a pulsed high voltage which may consist of voltage pulses of equal or alternating sign with respect to earth, which may thus either be a direct or an alternating voltage, a physical plasma can be generated at a small electric power, i.e. even without significant increase of temperature as compared to, for example, a sinusoidally modulated direct or alternating voltage. A cold plasma is desired in order to avoid thermal effects on the surface to the treated.

Practically, the pulses of the pulsed high voltage may have an average pulse spacing which is at least ten times, preferably at least hundred times and even more preferably at least thousand times as long as their average pulse duration. The average pulse spacing may be up to one hundred thousand times and even up to one million times as long as the average pulse duration.

Earthing of the object whose surface is treated with the device is not necessary, at least as long as the high voltage generator outputs pulses of alternating sign, i.e. an alternating voltage. Then, the capacitive electrical properties of the body, whose surface is to be treated, are sufficient for generating the electric discharges for plasma generation.

As already indicated, a device according to the present disclosure may advantageously be used as a hair loss therapy device. Then, it serves for treating a human scalp in order to dilate vessels located therein to excite a micro circulation and to increase the oxygen concentration such that hair growth is stimulated.

Referring now in greater detail to the drawings, the device 1 depicted in FIG. 1 comprises a base body 2. Within the base body 2, electrode bodies 3 are individually capacitively coupled to a high voltage bus 4; this is indicated by means of capacitor symbols. The high voltage bus 4 is connected to a high voltage terminal 5. In turn, the high voltage terminal 5 is connected to an output of a high voltage generator 6. In FIG. 1, the high voltage generator 6 is depicted within the base body 2; it may also be separated from the base body 2. At the high voltage terminal 5, the high voltage generator 6 generates a pulsed high voltage with respect to earth, whose pulses have alternating signs of the high voltage. The electrode bodies 3 lead out of the base body 2. They are oriented in parallel to one another and elongated towards distal ends 7. At the distal ends 7, spacers 8 are arranged. The spacers 8 consist of dielectric. Via the spacers 8, the electrode bodies 3 abut against a surface 9 to be treated of an objected 10, here of a scalp 11. Projections 13 of the spacers 8 beyond the exposed electrode surfaces 12 define the distances of the exposed electrode surfaces 12 to the surface 9, across which electric discharges 14 are generated by applying the pulsed high voltage. By means of the capacitive coupling of the electrode bodies 3 to the high voltage terminal 5 these electric discharges 14 are dielectrically restrained, i.e. they are dielectric barrier discharges. In the area of the electric discharges 14a physical plasma 15 is generated. The physical plasma 15 results in the desired treatment of the surface 9. Here, the drop-shaped spacers 8 also serve for a support of the electrode bodies 3 at the surface 9 without danger of injuries to the surface 9. The projections 13 are between 1.0 mm and 5.0 mm.

Figure 2:
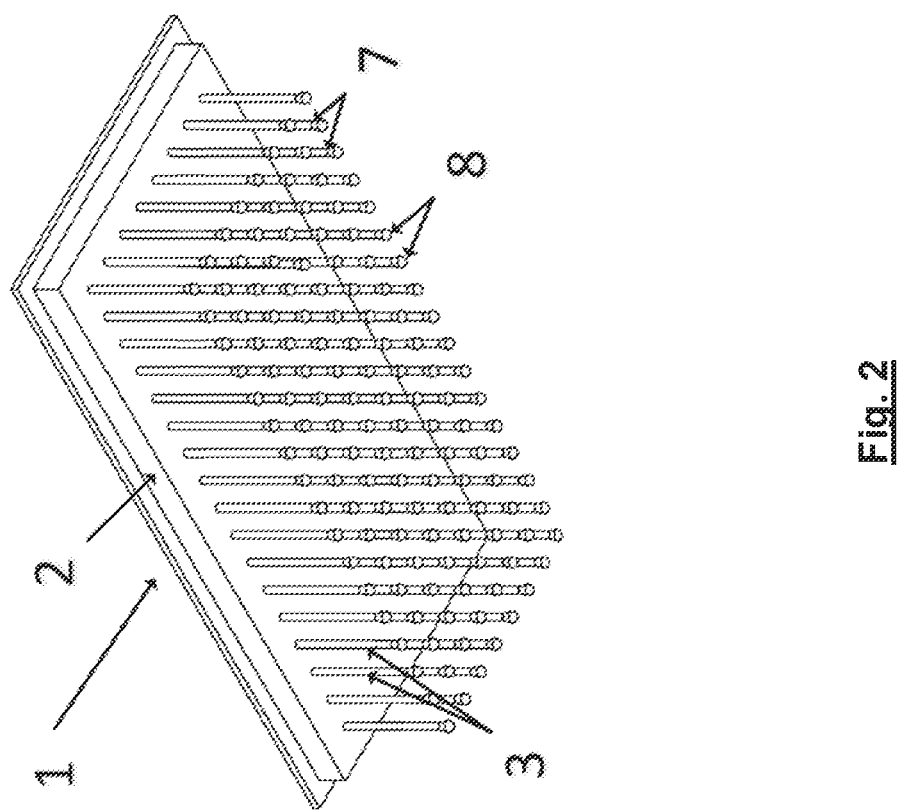
FIG. 2 is a perspective view of an exemplary embodiment of the device according to the invention.
Figure 3:
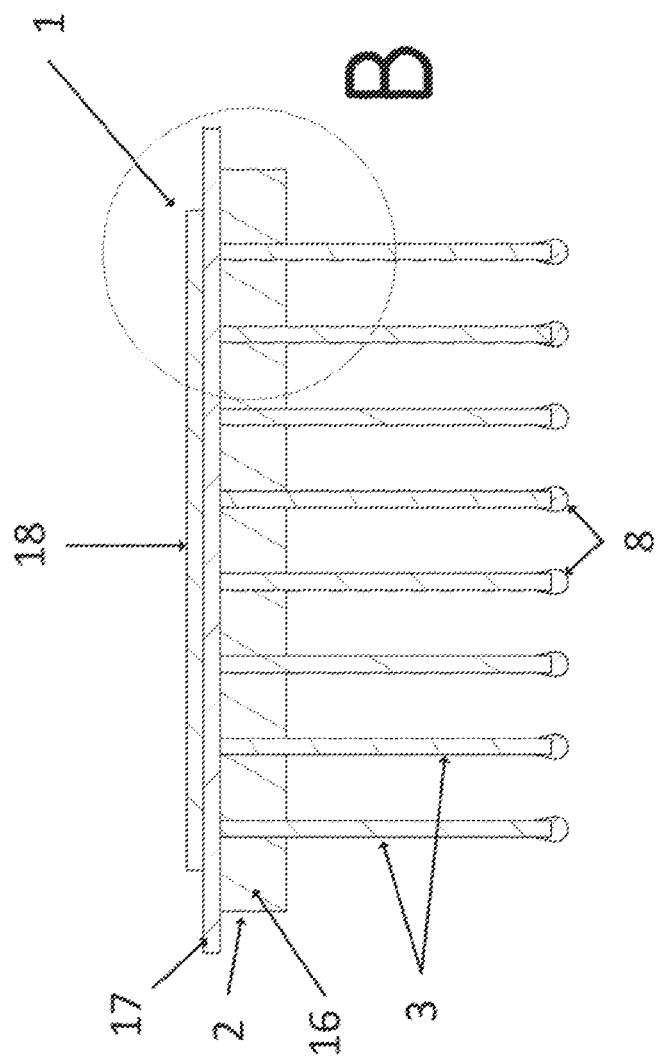
FIG. 3 is a section through the device according to FIG. 2.
Figure 4:
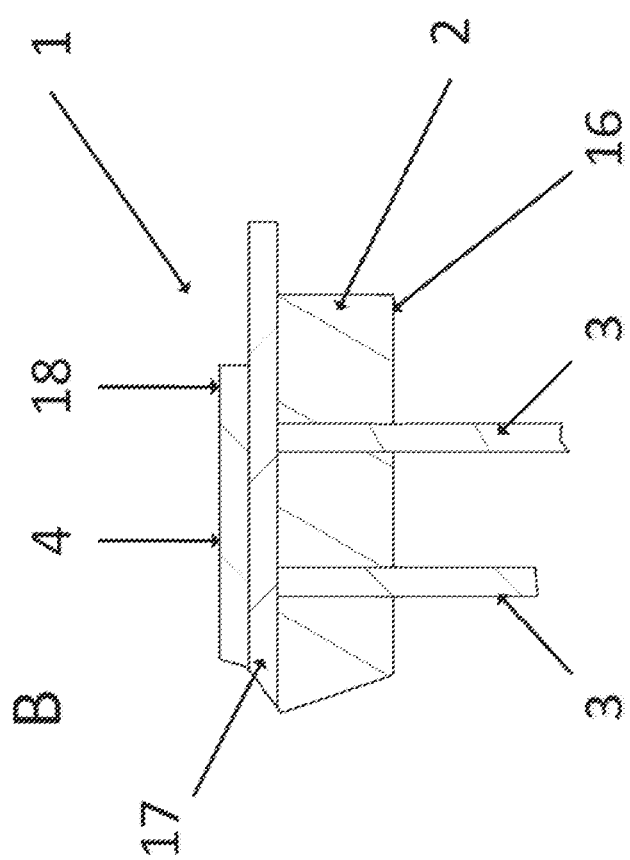
FIG. 4 is an enlarged detail of the device according to FIG. 2 which is indicated in FIG. 3 with a circle.

FIG. 2 shows that the electrode bodies 3 of the device 1 may be arranged in a two dimensional array in the way of the bristles of a brush. In this arrangement, the distal ends 7 and the, here spherical, spacers 8, respectively, are each arranged in a plane parallel to the base body 2. The section according to FIG. 3 and its enlarged detail according to FIG. 4 show that the individual electrode bodies 3 are mounted in parallel to one another in a plate 16 made of dielectric and extend up to a continuous layer 17 also made of dielectric. Behind the continuous layer 17a further continuous layer 18 made of metal is arranged which serves as the high voltage bus 4. Across the layer 17 the electrode bodies 3 are capacitively coupled to the high voltage bus 4. In the embodiment example depicted, the electrode bodies 3 have a diameter of about 1 mm and a lateral distance or spacing of about 5 mm. The free lengths of the electrode bodies 3 outside of the base body 2 up to the spacers 8 are about 20 to 25 mm. A diameter of the, here spherical, spacers 8 is 2 to 3 mm.

Many variations and modifications may be made to the preferred embodiments of the invention without departing substantially from the spirit and principles of the invention. All such modifications and variations are intended to be included herein within the scope of the present invention, as defined by the following claims.

We claim:

1. A device for generating physical plasma by means of dielectric barrier discharges with respect to a surface of an object, the device comprising
   a common high voltage terminal,
   a plurality of electrode bodies
   that are capacitively coupled to the common high voltage terminal,
   that comprise an exposed electrode surface and a distal end each, and
   that are, in a main extension direction, elongated in parallel to one another towards their distal ends, and
   spacers made of dielectric that are connected to the distal ends of the electrode bodies, the spacers projecting beyond the exposed electrode surfaces of the electrode bodies by 1.0 mm to 5.0 mm in the main extension direction.

2. The device of claim 1, wherein the spacers are arranged on top of the distal ends of the electrode bodies.

3. The device of claim 1, wherein the spacers enclose the distal ends of the electrode bodies.

4. The device of claim 1, wherein the spacers are spherical or drop-shaped.

5. The device of claim 1, wherein the spacers end with surface curvature radiuses which are at least as long as diameters of the exposed electrode surfaces of the electrode bodies.

6. The device of claim 5, wherein the diameters of the exposed electrode surfaces of the electrode bodies are in a range from 0.5 mm to 2.5 mm.

7. The device of claim 1, wherein the electrode bodies have free lengths in a range from 5.0 mm to 50 mm.

8. The device of claim 1, wherein the electrode bodies are elastic and support the spacers at bending stiffnesses in a range from 600 $Nmm^2$ to 4,000 $Nmm^2$.

9. The device of claim 1, wherein the electrode bodies are arranged at lateral distances in a range from 2.0 mm to 20 mm.

10. The device of claim 1, wherein the spacers are arranged in a one dimensional array along a straight line or a line with a steady course.

11. The device of claim 1, wherein the spacers are arranged in a two dimensional array along a plane or an area with a steady course.

12. The device of claim 1, comprising a base body, wherein the electrode bodies are mounted in the base body and capacitively coupled to the common high voltage terminal within the base body.

13. The device of claim 1, comprising a high voltage generator having an output and configured for outputting a pulsed high voltage with respect to earth at the output, wherein the common high voltage terminal is connected to the output of the high voltage generator.

14. The device of claim 13, wherein the pulsed high voltage is a direct voltage or an alternating voltage.

15. The device of claim 13, wherein pulses of the pulsed high voltage have an average pulse spacing which is 10 times to 1,000,000 times as long as an average pulse duration of the pulses.

16. A hair loss therapy apparatus comprising a device of claim 1.

* * * * *